US006410798B2

(12) United States Patent
Maassen et al.

(10) Patent No.: US 6,410,798 B2
(45) Date of Patent: Jun. 25, 2002

(54) PROCESS FOR THE PREPARATION OF 2,3, 5-TRIMETHY1-P-BENZOQUINONE

(75) Inventors: Ralf Maassen, Hanau; Steffen Krill, Speyer; Klaus Huthmacher, Gelnhausen, all of (DE)

(73) Assignee: Degussa-Huls Aktiengesellschaft, Frankfurt am Main (DE)

( * ) Notice: Subject to any disclaimer, the term of this patent is extended or adjusted under 35 U.S.C. 154(b) by 0 days.

(21) Appl. No.: 09/801,092

(22) Filed: Mar. 8, 2001

(30) Foreign Application Priority Data

Mar. 9, 2000 (DE) .......................... 100 11 405

(51) Int. Cl.[7] .................. C07C 45/00; C07C 49/105
(52) U.S. Cl. ........................ 568/358; 568/377
(58) Field of Search .................. 568/358, 362, 568/377; 362/377; 552/310

(56) References Cited

U.S. PATENT DOCUMENTS 5,041,572 A   8/1991   Hoercher et al.

6,262,311 B1 * 7/2001 Maassen et al. ............ 568/358

FOREIGN PATENT DOCUMENTS

EP    0 387 820    9/1990

OTHER PUBLICATIONS

Shimizu et al., "Synthesis of alkyl substituted p–benzoquinones from the corresponding phenols using molecular oxygen catalyzed by copper(II) chloride–amine hydrochloride systems", Bull. Chem. Soc. Jpn., 65, 1992, p. 1522–1526.
English language abstract of reference OR above; Derwent Accession No. 1990–284063/199038.

* cited by examiner

Primary Examiner—Alton Pryor
(74) Attorney, Agent, or Firm—Pillsbury Winthrop LLP

(57) ABSTRACT

A process for the preparation of 2,3,5-trimethyl-p-benzoquinone by oxidation of 2,3,5- or 2,3,6-trimethylphenol using oxygen or a gas mixture containing oxygen in the presence of a two-phase liquid reaction medium composed of water and a neocarboxylic acid having to 11 carbon atoms with a copper (II) halide-containing catalyst system at elevated temperature.

10 Claims, No Drawings

PROCESS FOR THE PREPARATION OF 2,3,5-TRIMETHY1-P-BENZOQUINONE

This application claims priority from German Application No. DE 100 11 405.9, filed on Mar. 9, 2000, the subject matter of which is hereby incorporated herein by reference.

BACKGROUND OF THE INVENTION

1. Field of the Invention

The present invention relates to a new process for the preparation of 2,3,5-trimethyl-p-benzoquinone by oxidation of 2,3,5- or 2,3,6-trimethylphenol using oxygen or a gas mixture containing oxygen in the presence of a two-phase liquid reaction medium composed of water and a neocarboxylic acid having 8 to 11 carbon atoms with a catalyst system containing copper(II)halide at elevated temperature.

2. Background Information 2,3,5-Trimethyl-p-benzoquinone is an intermediate which is used, inter alia, for the preparation of α-tocopherols (vitamin E).

The oxidation of trimethylphenols to 2,3,5-trimethyl-p-benzoquinone is well known.

Of the many processes described, oxidation using oxygen or a gas mixture containing oxygen with catalysis by copper salt-containing catalyst systems in two-phase liquid reaction media is of particular industrial interest. The advantage of these processes, apart from the excellent yields and selectivities which may be obtained, lies mainly in the use of an inexpensive and simple to prepare catalyst system which is present in the aqueous phase and may thus be separated after the reaction from the organic phase containing the product by simple phase separation and recycled with minimal expenditure and practically without loss of activity and selectivity.

According to EP 0 127 888, the oxidation of trimethylphenol to trimethyl-p-benzoquinone can be achieved in good yields using molecular oxygen in the presence of a separately prepared alkali metal or ammonium halogen cuprate of the copper oxidation state+2, optionally with the addition of an alkali metal or ammonium halide. A mixture of water and an aliphatic alcohol having four to ten carbon atoms is described here as the reaction medium. According to EP 0 167 153, the trimethyl-p-benzoquinone yield can be further increased and the formation of by-products further reduced if catalytic amounts of copper (I) hydroxide and/or copper (I) chloride are added additionally to the alkali metal or ammonium halogen cuprate described, and the alcoholic trimethylphenol solution is fed slowly to the aqueous catalyst solution.

EP 0 294 584 describes a process for the oxidation of trimethylphenol to trimethyl-p-benzoquinone by molecular oxygen using an aqueous solution of copper (II) chloride and lithium chloride as catalyst. A mixture of an aromatic hydrocarbon, preferably benzene, toluene, xylene or chlorobenzene, and a lower aliphatic alcohol having one to four carbon atoms is used as the solvent for the starting product and thus as the second liquid phase.

According to EP 0 475 272, alkaline earth halides as an aqueous solution in combination with copper (II) chloride may catalyse the described reaction efficiently instead of lithium chloride. Suitable organic solvents include both aliphatic alcohols having five to ten carbon atoms and mixtures of aromatic hydrocarbons and aliphatic alcohols having one to four carbon atoms.

EP 0 369 823 describes the oxidation of trimethylphenol to trimethyl-p-benzoquinone using a catalyst system which additionally contains, apart from copper (II) chloride, a salt of a hydroxylamine, oxime or amine with an inorganic acid, or a free oxime. The organic phase used in this process is either aliphatic alcohols having four to ten carbon atoms or mixtures of aromatic hydrocarbons and aliphatic alcohols having one to six carbon atoms.

A disadvantage of all the processes described is that the reaction is carried out at temperatures above or only just below the flash point of the solvents used. The associated risk of explosion conceals enormous risks for the industrial implementation of the processes, mainly because, on account of the need for the presence of molecular oxygen as oxidising agent, it is not possible to render the reaction mixture inert, this being otherwise customary when operating near or above the flash point of the solvent used. It is therefore absolutely vital, for the reaction described, to provide a sufficient safety margin between the reaction temperature and the flash point of the organic constituents so that a safe method of operating the plant can be guaranteed even in the event of temperature rises due to a short-term uncontrolled course of the reaction or in the event of technical plant problems. Without exception, this is not the case in the processes described. The preferred reaction temperatures in question of 60° C. or above which are required in order to obtain good yields are either above or only just below the flash points of the organic solvents described (cf. Table 1).

TABLE 1

| Solvent | Flash point [° C.] |
| --- | --- |
| Methanol | 11 |
| Ethanol | 12 |
| 1-Propanol | 15 |
| 1-Butanol | 30 |
| 1-Pentanol | 47 |
| 1-Hexanol | 60 |
| 1-Heptanol | 73 |
| 1-Octanol | 81 |
| 1-Nonanol | 75 |
| 1-Decanol | 82 |
| Benzene | −11 |
| Toluene | 6 |
| p-Xylene | 25 |
| Chlorobenzene | 28 |

This problem of conducting the reaction in an unsafe manner is discussed for the first time in EP 0 387 820. The solution to the problem described is the use of aliphatic alcohols having twelve to eighteen carbon atoms and flashpoints above 120° C. as the organic solvent with the use of copper (II) halide in combination with alkali or alkaline earth halides in the form of an aqueous solution as the catalyst of the reaction. At the preferred reaction temperatures from 80° C. to 90° C., the risk of explosion of the reaction mixture is thus reliably avoided with slightly reduced trimethyl-p-benzoquinone yields. A further advantage of the long-chain alcohols used lies in their high boiling point which is markedly above that of trimethyl-p-benzoquinone. As a result, the reaction product may be isolated easily by distillation from the crude product mixture, after phase separation, as a low-boiling product. A disadvantage of the alcohols used having twelve to eighteen carbon atoms, however, is their relatively high melting point (Table 2). These compounds are thus present as waxy solids at room temperature which entails several problems in relation to the industrial execution of the process. The solvent has to be melted first before the reaction commences, which means an additional process step and expenditure of energy. In addition, care has to be taken at not inconsiderable expense to ensure that all parts of the plant are kept at a temperature above the melting point of the alcohol at all times, even in the event of technical faults, since otherwise there is a risk of the organic phase solidifying in the plant and thus of plant parts becoming blocked.

TABLE 2

| Solvent | Flash point [° C.] | Melting point [° C.] |
|---|---|---|
| 1-Dodecanol | 127 | 22–24 |
| 1-Tetradecanol | 141 | 37–39 |
| 1-Hexadecanol | 135 | 49 |
| 1-Octadecanol | 192 | 55–58 |

SUMMARY OF THE INVENTION

It is therefore an object of the present invention to provide a process on the basis of the prior art which permits the oxidation of trimethylphenol to trimethyl-p-benzoquinone in good yields and with the reliable exclusion of the risk of explosion of the reaction mixture, and at the same time avoids the disadvantages of the existing processes listed in the assessment of the prior art.

It has now been found that this object can be achieved if a mixture of water and a neocarboxylic acid having 8 to 11 carbon atoms, preferably neodecanoic acid, is used as the solvent system, more particularly if the catalysts used are copper (II) halides to which alkaline earth, alkali or transition metal halides or halides of an element of the rare earths are added to increase the activity.

Neodecanoic acid denotes a mixture of octanoic, nonanoic and decanoic acid (producer: Exxon Chemical).

This result was surprising in so far as neodecanoic acid with <0.01 wt. % has a very low solubility in water, so it was to be expected that the aqueous catalyst phase would exhibit poor interaction with the organic substrate phase and also that neodecanoic acid would thus be relatively unsuitable for oxidation in the two-phase system.

It became apparent, however, that the oxidation of trimethylphenol to trimethyl-p-benzoquinone in the presence of a reaction medium composed of water and neodecanoic acid and with catalysis by means of a catalyst system containing at least copper (II) halide takes place in a very advantageous manner. The preferred reaction temperatures from 50° C. to 100° C., preferably from 60° C. to 90° C., are markedly below the flash point of the solvent, namely 122° C., so it can be safely guaranteed that oxidation is carried out with the exclusion of risks of explosion.

Due to the poor water solubility of neodecanoic acid, the aqueous catalyst phase may be separated easily from the organic phase containing the product by phase separation after the reaction has been completed. The catalyst phase may thus be recycled at minimum expense and reused many times without any significant loss of activity or selectivity.

The relatively high boiling point of neodecanoic acid (243° C. to 253° C.) compared with trimethyl-p-benzoquinone (198° C.) also permits simple and careful isolation, by distillation, of the heat-sensitive product from the crude product mixture as a low-boiling product and allows the neocarboxylic acid to be returned easily to the reaction.

The particular advantage of neodecanoic acid compared with the relatively long-chain alcohols having 12 to 18 carbon atoms known from the prior art lies, however, in the very low melting point of −39° C., as a result of which the sometimes serious disadvantages described in the assessment of the prior art as regards melting the solvent and avoiding the risk of plant parts becoming block are avoided.

The invention provides, therefore, a process for the preparation of 2,3,5-trimethyl-p-benzoquinone by oxidation of 2,3,5- or 2,3,6-trimethylphenol using oxygen or a gas containing oxygen in a two-phase liquid reaction medium using a catalyst containing at least copper (II) halide at elevated temperature, characterised in that the reaction is carried out in a mixture composed of water and neodecanoic acid and at temperatures from 50° C. to 100° C.

In the process according to the invention, one or more compounds from the class comprising alkali, alkaline earth or transition metal halides or the halides of the elements of the rare earths may be added to the copper (II) halide in order to increase the catalyst activity.

Suitable copper (II) halides include substantially copper (II) chloride and copper (II) bromide. The alkali, alkaline earth and transition metal halides and halides of an element of the rare earths added to increase the activity are preferably lithium chloride, sodium chloride, magnesium chloride, calcium chloride, chromium (III) chloride and cerium (III) chloride.

The aqueous catalyst phase is prepared by simply mixing the aqueous solutions of the individual components or by dissolving the solid salt compounds in water, which markedly simplifies the process.

The molar ratio of the copper (II) halide with respect to trimethylphenol may vary widely and is usually copper salt/trimethylphenol=0.1–10, preferably 0.2–3.

The halides added to increase the activity of the catalyst may be used in 0.1 to 12 times the molar amount, relative to trimethylphenol, 0.2 to 8 times the molar amount being preferred. The concentration of the copper halide in the aqueous catalyst phase may range from 1 wt. % to 70 wt. %, concentrations from 5 wt. % to 30 wt. % being preferred, and the activity-increasing halides are used preferably in a concentration range from 5 wt. % to 80 wt. %.

The systems well known from the prior art are used as additional activators of the reaction, and copper salts such as copper (I) chloride or the corresponding hydroxide are used most advantageously.

The oxidising agent used in the process according to the invention is oxygen in the pure form or dilute form, e.g., air. As a rule, 10 to 150 $L_n$ of gaseous oxygen per hour are added, based on 1 L of reaction mixture. The new process is usually carried out at normal pressure. The process may also be carried out under pressure; a pressurised mode of operation is particularly suitable in the case of gas mixtures containing oxygen. It may be carried out both continuously and batchwise.

In order to carry out the reaction, trimethylphenol is dissolved in neodecanoic acid and fed to the aqueous phase containing the catalyst. In another embodiment, a part of the organic solvent is charged with the aqueous phase before the reaction commences and the trimethylphenol solution is added. In yet another variant of the reaction procedure, the reaction is carried out batchwise by charging all the components, with stirring, and then starting to add the gas containing oxygen.

The trimethylphenol concentration in the organic phase may be varied within wide concentration ranges; trimethylphenol concentrations from 5 wt. % to 80 wt. % are generally obtained, preferably concentrations from 10 wt. % to 50 wt. %.

The ratio of volumes of water to organic solvent may range from 10:1 to 1:10, a range from 3:1 to 1:5 being preferred.

The reaction temperature may vary over a wide temperature interval, and the reaction is carried out preferably at a temperature from 50° C. to 100° C., operations being carried out at a temperature from 60° C. to 90° C. in a particularly preferred embodiment.

The reaction product 2,3,5-trimethyl-p-benzoquinone may be isolated in the usual way, for example, by vacuum or steam distillation.

The process according to the invention is simple to carry out and provides the reaction product in a good yield and in good purity.

According to Example 16, the recovered catalyst solution may be used again many times without loss of yield.

The yield determinations were carried out on an HPLC system from Jasco comprising a UV detector UV 975, a pump PU 980 and an autosampler AS 950. The column used was an Inertsil-ODS 3V-5µ, internal diameter 250×4.6 mm, from GL Sciences Inc. The external standard used was trimethyl-p-benzoquinone which was purified by distillation and repeated crystallization.

DETAILED DESCRIPTION OF THE INVENTION

The following examples are provided to explain the invention in more detail, but are not intended to limit the invention.

TMP stands for 2,3,6-trimethylphenol.

TMQ stands for 2,3,5-trimethyl-p-benzoquinone.

EXAMPLES 1 TO 15

Copper (II) chloride and an alkali, alkaline earth or transition metal halide were charged to a glass reactor as a saturated aqueous solution in the amounts shown in Table 3, neodecanoic acid was added in the amount indicated in each case, and the mixture was heated to the reaction temperature shown in Table 3. A solution of 24 g of TMP (176 mmole) in 120 mL of neodecanoic acid was then added dropwise by way of a frit within a period of 3 hours, with stirring (800 rpm) and introduction of oxygen (Example 7: immediate addition of the entire amount; batch preparation). After the addition was complete, stirring was continued for another 3 h (Example 1: 4 h; Example 14: 5 h) at the temperature indicated, with the introduction of oxygen, and the course of the reaction was monitored by HPLC. After the reaction had ended, the phases were separated, the organic phase was washed twice with saturated sodium chloride solution and the TMQ yield was determined by HPLC with the external standard.

TABLE 3

| Example | Catalyst (molar amount [mmole]) | Stoichiometry TMP/CuCl$_2$/halide | Temperature [° C.] | Amount of neodecanoic acid charged [mL] | TMQ-yield [%] |
| --- | --- | --- | --- | --- | --- |
| 1 | CuCl$_2$ (176) LiCl (704) | 1:1:4 | 60 | 0 | 88.9 |
| 2 | CuCl$_2$ (132) LiCl (528) | 1:0.75:3 | 70 | 0 | 89.5 |
| 3 | CuCl$_2$ (176) LiCl (704) | 1:1:4 | 70 | 0 | 90.9 |
| 4 | CuCl$_2$ (176) | 1:1:4 | 70 | 30 | 91.2 |
| 5 | CuCl$_2$ (88) LiCl (352) | 1:0.5:2 | 80 | 0 | 84.8 |
| 6 | CuCl$_2$ (132) LiCl (528) | 1:0.75:3 | 80 | 0 | 87.3 |
| 7 | CuCl$_2$ (132) LiCl (528) | 1:0.75:3 | 80 | 0 | 87.2 |
| 8 | CuCl$_2$ (176) LiCl (704) | 1:1:4 | 80 | 0 | 90.2 |
| 9 | CuCl$_2$ (132) LiCl (528) | 1:0.75:3 | 90 | 0 | 86.4 |
| 10 | CuCl$_2$ (132) LiCl (528) | 1:0.75:3 | 90 | 30 | 87.4 |
| 11 | CuCl$_2$ (132) LiCl (528) | 1:0.75:3 | 90 | 60 | 87.3 |
| 12 | CuCl$_2$ (176) LiCl (704) | 1:1:4 | 90 | 0 | 89.8 |
| 13 | CuCl$_2$ (176) MgCl$_2$ (352) | 1:1:2 | 90 | 0 | 89.0 |
| 14 | CuCl$_2$ (176) CrCl$_3$ (352) | 1:1:2 | 90 | 0 | 92.3 |
| 15 | CuCl$_2$ (132) LiCl (528) | 1:0.75:3 | 100 | 0 | 88.5 |

EXAMPLE 16

The execution of the reaction according to embodiment 3 was repeated, water of reaction additionally produced by the oxidation reaction being removed from the catalyst solution obtained after phase separation by concentration in a rotary evaporator. The aqueous catalyst solution thus obtained was used again directly in the reaction without further treatment and the procedure was carried out a total of six times in succession. The TMQ yield thus obtained after the fifth re-use of the original catalyst solution was 89.7%.

What is claimed is:

1. A process for the preparation of 2,3,5-trimethyl-p-benzoquinone by oxidation of 2,3,5- or 2,3,6-trimethylphenol using oxygen or a gas containing oxygen in a two-phase liquid reaction medium using a catalyst containing at least copper (II) halide at elevated temperature, wherein the reaction is carried out in a mixture composed of water and a neocarboxylic acid having 8 to 11 carbon atoms and at temperatures from 50° C. to 100° C.

2. A process for the preparation of 2,3,5-trimethyl-p-benzoquinone according to claim 1, wherein the neocarboxylic acid is neodecanoic acid and isomers thereof.

3. A process for the preparation of 2,3,5-trimethyl-p-benzoquinone according to claim 1, wherein the reaction is carried out in the presence of said copper (II) halide and an alkali halide as catalyst system.

4. A process for the preparation of 2,3,5-trimethyl-p-benzoquinone according to claim 3, wherein the alkali halide is lithium chloride or sodium chloride.

5. A process for the preparation of 2,3,5-trimethyl-p-benzoquinone according to claim 1, wherein the reaction is carried out in the presence of said copper (II) halide and an alkaline earth halide as catalyst system.

6. A process for the preparation of 2,3,5-trimethyl-p-benzoquinone according to claim 5, wherein the alkaline earth halide is magnesium chloride or calcium chloride.

7. A process for the preparation of 2,3,5-trimethyl-p-benzoquinone according to claim 1, wherein the reaction is carried out in the presence of said copper(II)halide and a transition metal halide as catalyst system.

8. A process for the preparation of 2,3,5-trimethyl-p-benzoquinone according to claim 7, wherein the transition metal halide is chromium(III)chloride.

9. A process for the preparation of 2,3,5-trimethyl-p-benzoquinone according to claim 1, wherein the reaction is carried out in the presence of said copper (II) halide and a halide of an element of the rare earths as catalyst.

10. A process for the preparation of 2,3,5-trimethyl-p-benzoquinone according to claim 9, wherein the halide of an element of the rare earths used is cerium (III) chloride.

* * * * *